United States Patent
Sukuru

(10) Patent No.: US 8,333,989 B2
(45) Date of Patent: Dec. 18, 2012

(54) HYDROPHILIC VEHICLE-BASED DUAL CONTROLLED RELEASE MATRIX SYSTEM

(75) Inventor: Karunakar Sukuru, High Point, NC (US)

(73) Assignee: Banner Pharmacaps, Inc., High Point, NC (US)

( * ) Notice: Subject to any disclaimer, the term of this patent is extended or adjusted under 35 U.S.C. 154(b) by 620 days.

(21) Appl. No.: 11/553,356

(22) Filed: Oct. 26, 2006

(65) Prior Publication Data

US 2007/0098783 A1  May 3, 2007

Related U.S. Application Data

(60) Provisional application No. 60/730,406, filed on Oct. 26, 2005.

(51) Int. Cl.
*A61K 9/66* (2006.01)

(52) U.S. Cl. ...................................... 424/452

(58) Field of Classification Search .................. None
See application file for complete search history.

(56) References Cited

U.S. PATENT DOCUMENTS

| | | | | |
|---|---|---|---|---|
| 3,947,600 | A * | 3/1976 | Rousseau | 426/302 |
| 5,447,729 | A | 9/1995 | Belenduik et al. | |
| 5,498,422 | A | 3/1996 | Nakamichi et al. | |
| 5,609,882 | A | 3/1997 | Aoki et al. | |
| 6,027,746 | A | 2/2000 | Lech | |
| 6,251,426 | B1 | 6/2001 | Gullapalli | |
| 2001/0004459 | A1 | 6/2001 | Barthelemy et al. | |
| 2002/0160041 | A1 | 10/2002 | Gutierrez-Rocca | |
| 2003/0091603 | A1 * | 5/2003 | Ohmori et al. | 424/401 |
| 2003/0203030 | A1 * | 10/2003 | Ashton et al. | 424/484 |
| 2004/0033257 | A1 | 2/2004 | Iyer et al. | |
| 2004/0052731 | A1 | 3/2004 | Hirsh et al. | |
| 2005/0152968 | A1 | 7/2005 | Brophy et al. | |
| 2006/0286172 | A1 * | 12/2006 | Mahashabde | 424/488 |

FOREIGN PATENT DOCUMENTS

| | | |
|---|---|---|
| AU | 199719991 | 11/1997 |
| GB | 2283172 | 5/1995 |
| GB | 2283172 A * | 5/1995 |
| GB | 2331458 | 5/1999 |
| WO | WO 99/36060 | 7/1999 |
| WO | WO 01/22942 | 4/2001 |
| WO | WO 01/34119 | 5/2001 |
| WO | WO02/11701 | 2/2002 |
| WO | WO 02/083177 | 10/2002 |
| WO | WO 02083177 A1 * | 10/2002 |
| WO | WO 03/086392 | 10/2003 |
| WO | WO 2004/030658 | 4/2004 |
| WO | WO 2005/009409 | 2/2005 |
| WO | WO 2005/041929 | 5/2005 |

OTHER PUBLICATIONS

Methocel™ Product literature (Introducing Methocel™ DC Grade Hypromellose Polymers for Direct Compression of Controlled Release Dosage Forms, Dow Chemical Company, Oct. 2008).*
Al-Gohary (Pharmaceutica Acta Helvetiae 1997, 72, 81-86).*
PubMed Health (Misoprostol, US National Library of Medicine, NIH 2008).*
(Msn encarta; definition: including acessed May 23, 2011).*

* cited by examiner

*Primary Examiner* — Johann Richter
*Assistant Examiner* — Jessica Kassa
(74) *Attorney, Agent, or Firm* — Pabst Patent Group LLP

(57) ABSTRACT

A hydrophilic vehicle-based dual controlled-release matrix system, suitable for encapsulation in hard or soft capsules, has been developed. The matrix is in the form of a solution or a suspension, which allows for easier formulation of low dose compounds. The matrix includes two rate controlling barriers for the controlled release of one or more pharmaceutically active agents. The primary rate controlling barrier includes a hydrophilic vehicle. The primary rate controlling barrier can further comprise one or more solvents which are miscible with the hydrophilic vehicle. The secondary rate controlling barrier includes a hydrogel-forming polymeric material dissolved or dispersed in the hydrophilic vehicle. The presence of the hydrogel-forming polymeric material makes extraction of the drug from the dosage form more difficult. This feature could be beneficial in preventing or minimizing the misuse of dosage forms which contain drugs which are prone to abuse.

15 Claims, 3 Drawing Sheets

HYDROPHILIC VEHICLE-BASED DUAL CONTROLLED RELEASE MATRIX SYSTEM

Priority is claimed to U.S. application Ser. No. 60/730,406, filed Oct. 26, 2005.

FIELD OF THE INVENTION

The present invention is generally in the field of pharmaceutical compositions, specifically controlled release pharmaceutical compositions.

BACKGROUND OF THE INVENTION

Controlled release (CR) formulations are useful in situations where drug release over an extended period of time is required, such as repetitive, intermittent dosings of a drug from one or more immediate release systems. Controlled release drug delivery systems are used to improve the therapeutic response by providing blood levels that are more consistent and stable compared to immediate release dosage forms. Existing CR dosage forms are based on matrix tablets or coated tablets or capsules filled with coated drug particles or granules. These systems, however, have several drawbacks, including the lack of content uniformity and homogeneity, particularly with compounds present in low dosages. Moreover, low dose compounds, as well as compounds which are moisture sensitive, can be difficult to handle in powder form, which is the form typically used to prepare tablets or powder-filled hard gelatin capsules.

Controlled release formulations, particularly of drugs such as opioid analgesics which are prone to abuse, can be susceptible to misuse. Currently available sustained release formulations of such drugs, which contain a relatively large amount of drug meant to be released from the formulation over an extended time period, are particularly attractive to abusers since the sustained release action can be destroyed by crushing or grinding the formulation. The resulting material (i.e., the crushed formulation) can no longer control the release of drug. Depending on the drug, abusers can then (1) snort the material, (2) swallow the material or (3) dissolve the material in water and subsequently inject it intravenously. The dose of drug contained in the formulation is thus absorbed immediately through the nasal or GI mucosa (for snorting or swallowing, respectively) or is administered in a bolus to the systemic circulation (for IV injection). These abuse methods result in the rapid bioavailability of relatively high doses of drug, giving the abuser a "high". Since relatively simple methods (crushing, grinding, chewing and/or dissolution in water) can be used to transform such formulations into an abusable form, they provide virtually no deterrent to a potential abuser.

There is a need for a liquid controlled-release formulation is which low dose compounds can be more easily formulated.

There also is a need for a controlled release formulation which can minimize or prevent the misuse of drugs which are prone to abuse by making it more difficult for the drug to be extracted from the dosage form.

Therefore, it is an object of the invention to provide a dual controlled release liquid matrix for the formulation of low dose drugs, and methods of manufacture thereof.

It is further an object of the invention to provide a dual controlled release liquid matrix which can minimize or prevent the misuse of drugs which are prone to abuse.

BRIEF SUMMARY OF THE INVENTION

A hydrophilic vehicle-based dual controlled-release matrix system, suitable for encapsulation in hard or soft capsules, has been developed. The matrix is in the form of a solution or a suspension, which allows for easier formulation of low dose compounds. The matrix includes two rate controlling barriers for the controlled release of one or more pharmaceutically active agents. The primary rate controlling barrier includes a hydrophilic vehicle, such as a combination of high molecular weight and low molecular weight polyethylene glycols. The primary rate controlling barrier can further comprise one or more solvents which are miscible with the hydrophilic vehicle. The second rate controlling barrier includes a hydrogel-forming polymeric material dissolved or dispersed in the hydrophilic vehicle. Formation of the hydrogel can occur during drying when water migrates from the shell into the fill or upon dissolution of the capsule shell as the surrounding aqueous media comes into contact with the matrix. Polymer hydration and the subsequent swelling of the polymeric material controls release of the drug by diffusion through, and/or erosion of, the hydrogel. This system allows for the formation of a clear controlled release liquigel for drugs that are soluble in hydrophilic media. Judicious selection of the qualitative and quantitative composition of the polymer matrix allows one to modulate the release profile of the drug, including a biphasic drug release profile, for up to 24 hours. The use of a liquid matrix minimizes the problems associated with handling powders, such as content uniformity and homogeneity, as well as eliminates the need for organic solvents which are often required in the manufacture of tablets or powder-filled hard shell capsules.

The hydrogel-forming polymeric material, which forms a hydrogel upon contact with an aqueous solution, trapping the drug, makes extraction of the drug from the dosage form more difficult. This feature is beneficial in decreasing the misuse of dosage forms which contain drugs which are prone to abuse.

DETAILED DESCRIPTION OF THE INVENTION

Figure 1:
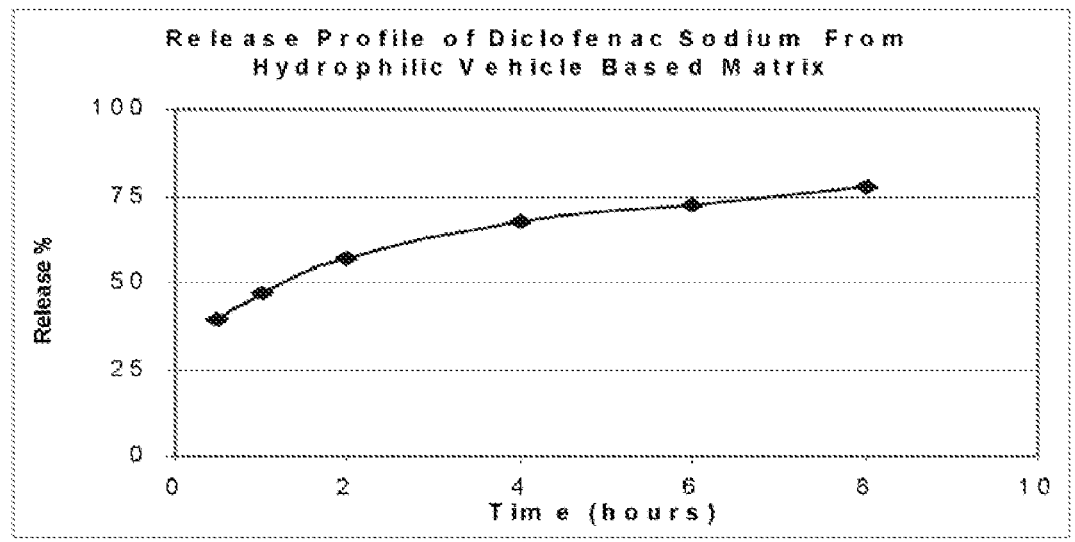
FIG. 1 shows the release profile of Diclofenac sodium (% Diclofenac sodium) versus time (hours) from a hydrophilic vehicle-based matrix system.

Liquid controlled release matrix systems suitable for encapsulation in a soft gelatin capsule, a non-animal soft shell capsule, or a liquid filled hard shell capsule, have been developed. The matrix includes a hydrogel-forming polymeric material dissolved or dispersed in a hydrophilic vehicle such as a combination of high and low molecular weight polyethylene glycols.

I. Dual Controlled Release Matrix

A. Definitions

As used herein, a "dual controlled-release matrix" refers to a matrix containing a primary rate controlling barrier and a secondary rate controlling barrier dissolved or dispersed in the primary rate controlling barrier. The primary rate controlling barrier includes a hydrophilic vehicle. The secondary rate controlling barrier includes a hydrogel-forming polymeric material. Formation of the hydrogel can occur during drying when water migrates from the shell into the fill or upon dissolution of the capsule shell as the surrounding aqueous media comes into contact with the matrix. Judicious selection of the qualitative and quantitative composition of the polymer matrix allows one to modulate the release profile of the drug, including a biphasic drug release profile, for up to 24 hours.

As used herein "hydrogel" refers to materials which swell extensively in water and slowly dissolve or erode with time depending on the viscosity and the molecular weight, but are not water soluble.

As used herein, "hydrophilic vehicle" refers to one or more compounds which have a strong affinity for water. Hydrophilic materials tend to dissolve in, mix with, or be wetted by water.

As used herein, a "biphasic release profile" refers to a drug release profile having two distinct phases or stages.

As used herein, "controlled release" refers to a release profile of a drug for which the drug release characteristics of time course and/or location are chosen to accomplish therapeutic or convenience objectives not offered by conventional dosage forms such as solutions, or promptly dissolving dosage forms. Delayed release, extended release, and pulsatile release and their combinations are types of controlled release.

B. Hydrophilic Vehicle

The hydrogel-forming polymeric material is dissolved or dispersed in a hydrophilic vehicle. Exemplary hydrophilic vehicles include, but are not limited to, polyethylene glycols, polyoxyethylene 32 lauric glycerides (available from Abitech under the tradename ACCONON® M-44), polyoxyethylene 8 caprylic/capric glycerides (available from Abitech under the tradename ACCONON® MC-8) and glycofurol. The hydrophilic vehicle is present in an amount from about 10 to about 80% by weight, preferably from about 20 to about 60% by weight, of the fill material. The hydrophilic vehicle can further comprise one or more miscible solvents such as glycerin (0-10% by weight of the matrix), propylene glycol (0-20% by weight of the matrix), ethanol (0-15% by weight of the matrix), glycofurol (0-80% by weight of the matrix) and caprylocaproyl macrogol-8 (0-50% by weight of the matrix; available from Gattefosse S.A., Saint Priest, France under the tradename LABRASOL®). Varying the qualitative and quantitative composition of the hydrophilic vehicle and the hydrogel-forming polymeric material allows one to modulate the release profile of the drug, including a biphasic drug release profile, for up to 24 hours.

C. Hydrogel-Forming Polymers

Exemplary hydrogel-forming polymer materials include, but are not limited to, cellulose ethers, preferably different viscosity/molecular weight grades of hypromelloses such as HPMC K4M to K100M which are available from Dow Chemical; cross-linked acrylates such as CARBOPOL® available from B.F. Goodrich Co.; alginates; guar or xanthan gum; carrageenan; polypyrrolidone; carboxymethylcellulose; and mixtures thereof. The hydrogel-forming polymeric material is dissolved in the hydrophilic vehicle provided the active agent is water soluble. If the active agent is water insoluble, the polymeric material is dispersed in the hydrophilic vehicle along with the drug. The hydrogel-forming polymeric material is present in an amount from about 3% to about 80% by weight preferably 5% to 50% by weight of the matrix. Incorporation of the drug into the hydrogel-forming polymeric material can protect the drug from exposure upon mechanical disruption, such as grinding, chewing or cutting and thus prevent or minimize misuse.

D. Active Agents

Most therapeutic, prophylactic and/or diagnostic agents can be encapsulated. Exemplary drug agents useful for forming the composition described herein include, but are not limited to, analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelminthic agents; antihistamines; antihyperlipidemic agents; antihypertensive agents; anti-infective agents; anti-inflammatory agents; antimigraine agents; antineoplastic agents; antiparkinson drugs; antipruritic agents; antipsychotic agents; antipyretic agents; antispasmodic agents; antitubercular agents; antiulcer agents; antiviral agents; anxiolytic agents; appetite suppressants (anorexic agents); attention deficit disorder and attention deficit hyperactivity disorder drugs; cardiovascular agents including calcium channel blocks, antianginal agents, central nervous system ("CNS") agents, beta-blockers and antiarrhythmic agents; central nervous system stimulants; diuretics; genetic materials; hormonolytics; hypnotics; hypoglycemic agents; immunosuppresive agents; muscle relaxants; narcotic antagonists; nicotine; nutritional agents; parasympatholytics; peptide drugs, psychostimulants, sedatives; sialagogues, steroids, smoking cessation agents; sympathomimetics; tranquilizers; vasodilators; beta-agonist, tocolytic agents, and combination thereof.

The active agents can be administered as the neutral acid or base or as pharmaceutically acceptable salt. As used herein, "pharmaceutically acceptable salts" refer to derivatives of the disclosed compounds wherein the parent compound is modified by making the acid or base addition salt thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, methanesulfonic, ethane disulfonic, oxalic, and isethionic.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704.

E. Carriers

Formulations may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients and the rate controlling compounds. As generally used herein "carrier" includes, but is not limited to, plasticizers, crystallization inhibitors, wetting agents, bulk filling agents, solubilizers, bioavailability enhancers, solvents, pH-adjusting agents and combinations thereof.

II. Capsule Shell Composition

A. Gelatin Capsules

Gelatin is the product of the partial hydrolysis of collagen. Gelatin is classified as either Type A or Type B gelatin. Type A gelatin is derived from the acid hydrolysis of collagen while Type B gelatin is derived from the alkaline hydrolysis of collagen. Traditionally, bovine bones and skins have been used as raw materials for manufacturing Type A and Type B gelatin while porcine skins have been used extensively for manufacturing Type A gelatin. In general acid-processed gelatins form stronger gels than lime-processed gelatins of the same average molecular weight. The capsules can be formulated as hard or soft gelatin capsules.

B. Non-gelatin Capsules

Non Gelatin Shell-Carrageenan

Carrageenan is a natural polysaccharide hydrocolloid, which is derived from sea weed. It includes a linear carbohydrate polymer of repeating sugar units, without a significant degree of substitution or branching. Most, if not all, of the galactose units on a carrageenan molecule possess a sulfate ester group. There are three main types of carrageenan: cappa, iota and lambda; although minor forms called mu and nu carrageenan also exist.

C. Shell Additives

Suitable shell additives include plasticizers, opacifiers, colorants, humectants, preservatives, flavorings, and buffering salts and acids.

Plasticizers are chemical agents added to gelatin to make the material softer and more flexible. Suitable plasticizers include, but are not limited to, glycerin, sorbitol solutions which are mixtures of sorbitol and sorbitan, and other polyhydric alcohols such as propylene glycol and maltitol or combinations thereof.

Opacifiers are used to opacify the capsule shell when the encapsulated active agents are light sensitive. Suitable opacifiers include titanium dioxide, zinc oxide, calcium carbonate and combinations thereof.

Colorants can be used to for marketing and product identification/differentiation purposes. Suitable colorants include synthetic and natural dyes and combinations thereof.

Humectants can be used to suppress the water activity of the softgel. Suitable humectants include glycerin and sorbitol, which are often components of the plasticizer composition. Due to the low water activity of dried, properly stored softgels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl esters (collectively known as "parabens") or combinations thereof.

Flavorings can be used to mask unpleasant odors and tastes of fill formulations. Suitable flavorings include synthetic and natural flavorings. The use of flavorings can be problematic due to the presence of aldehydes which can cross-link gelatin. As a result, buffering salts and acids can be used in conjunction with flavorings that contain aldehydes in order to inhibit cross-linking of the gelatin.

D. Enteric Coatings or Shell Additives

The capsules can be coated with an enteric coating, or, alternatively, an enteric polymer can be incorporated into the capsule shell. In a preferred embodiment using an enteric polymer, the capsule shell is prepared from a mass including a film-forming polymer, an acid insoluble polymer an aqueous solvent, and optionally a plasticizer. Suitable film-forming polymers include, but are not limited to, gelatin. Suitable acid-insoluble polymers include, but are not limited to, acrylic-acid/methacrylic acid copolymers. The acid-insoluble polymer is present in an amount from about 8% to about 20% by weight of the wet gel mass. The weight ratio of acid-insoluble polymer to film-forming polymer is from about 25% to about 50%. The aqueous solvent is water or an aqueous solution of alkalis such as ammonia or diethylene amine or hydroalcoholic solutions of the same. Suitable plasticizers include glycerin and triethylcitrate. Enteric capsule shells and a method of making the capsule shell are described in WO 2004/030658 to Banner Pharmacaps, Inc.

III. Method of Making

A. Dual Controlled Release Matrices

The dual controlled release matrix can be prepared using a hydrophilic vehicle that is a solid or a liquid at room temperature. If the hydrophilic vehicle is a solid at room temperature, it can be prepared by melting the hydrophilic vehicle to form a liquid base. Optionally, one or more surfactants or liquid excipients are added to the hydrophilic vehicle. In one embodiment, the active agent is first added to a hydrogel-forming polymeric material to form a secondary rate controlling barrier; and then the secondary rate controlling barrier is dissolved or dispersed in the hydrophilic vehicle. The secondary rate controlling barrier is dissolved or dispersed in the hydrophilic vehicle by mixing or homogenizing the hydrogel-forming polymeric material with the hydrophilic vehicle at a temperature above the congealing temperature of the hydrophilic vehicle. In some embodiments, the active agent is dissolved or dispersed in the hydrophilic vehicle separately from the hydrogel-forming polymeric material. The active agent is dissolved or dispersed in the hydrophilic vehicle by mixing or homogenization. The fill material, which includes the hydrophilic vehicle, the hydrogel-forming polymeric material and the active agent, is then dearated to remove any trapped air, such as by applying a vacuum or purging with another gas, prior to encapsulation.

B. Encapsulation of Dual Controlled Release Matrices

The deaerated fill material described above can be encapsulated at room temperature or at elevated temperatures (up to 35° C. for soft gelatin capsules and up to 60° C. for non-animal soft shell capsules) to facilitate the fill flow. Encapsulation in soft shell capsules is done using a rotary die encapsulation machine using standard procedures. The capsules are dried to the desired hardness and/or fill moisture content to facilitate the handling of the capsules during packaging, shipping, and storage.

Any active agent which requires controlled release can be encapsulated in the hydrophilic-based vehicle matrix with a fill weight range of 100 mg to 2200 mg in a capsule suitably sized for swallowing. The capsules are processed following standard procedures and can be packaged in either bottles or blisters packs.

EXAMPLES

Example 1

Preparation of a Diclofenac Sodium Fill Matrix

A hydrophilic vehicle-based dual controlled-release matrix system was prepared containing the following ingredients.

| Name of the ingredient | % wt. of fill matrix |
|---|---|
| Polyethylene glycol | 60 |
| CARBOPOL ® | 2.5 |
| Hypromellose | 10 |

| Name of the ingredient | % wt. of fill matrix |
|---|---|
| PVP K90 | 2.5 |
| Diclofenac sodium | 25 |

CARBOPOL® and PVP K90 were dispersed in liquefied/melted polyethylene glycol just above its congealing temperature while mixing with a suitable mixer. Hypromellose was added to the mixture with stirring. Diclofenac sodium was then added to the mixture with continuous stirring. The blend was homogenized and deaerated prior to encapsulation in soft gelatin capsules. The same procedure was used to prepare the diltiazem and ibuprofen fill matrix preparations.

In vitro drug release studies were conducted using a USP dissolution apparatus II (paddles) at 50 rpm. The results are shown in FIG. 1. Experiments were conducted in dissolution media at a temperature of 37.0±0.5° C. for 8 hours in 6.8 phosphate buffer. Samples were periodically withdrawn and analyzed for diclofenac content using the ultraviolet ("UV") method. The samples were analyzed at a wavelength of 276 nm.

Example 2

Preparation of a Diltiazem Hydrochloride Fill Matrix

A hydrophilic vehicle-based dual controlled-release matrix system was prepared containing the following ingredients

| Name of the ingredient | % wt. of fill matrix |
|---|---|
| Polyethylene glycol | 60 |
| Hypromellose | 9.3 |
| CARBOPOL ® | 1.1 |
| PVPK90 | 1.6 |
| Diltiazem HCl | 28 |

Figure 2:
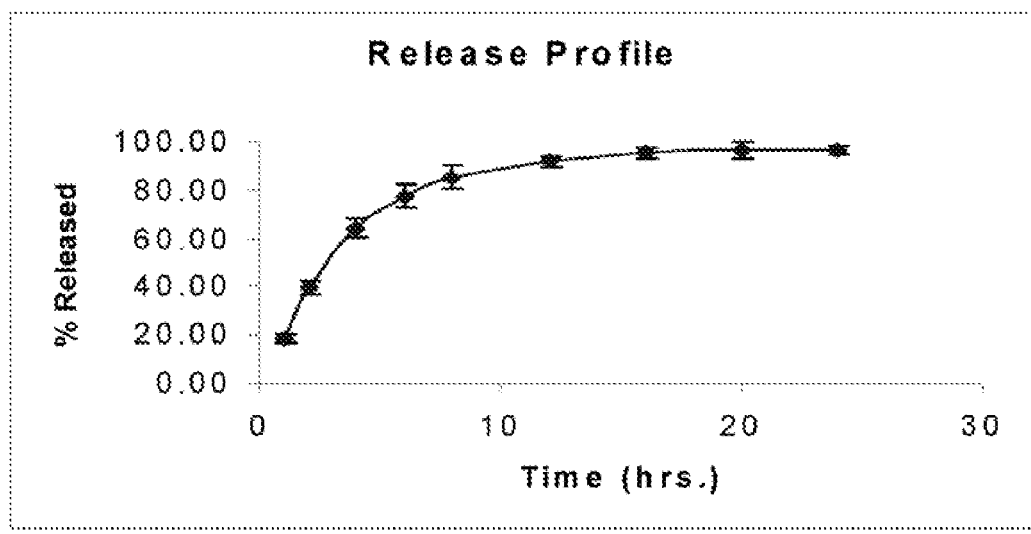
FIG. 2 shows the release profile of Diltiazem hydrochloride (% Diltiazem hydrochloride) versus time (hours) from a hydrophilic vehicle-based matrix system.

In vitro drug release studies were conducted using a USP dissolution apparatus II (paddles) at 100 rpm. The results are shown in FIG. 2. Experiments were conducted in dissolution media at a temperature of 37.0±0.5° C. for 24 hours in 6.5 phosphate buffer. Samples were periodically withdrawn and analyzed for diltiazem hydrochloride content using the ultraviolet ("UV") method. The samples were analyzed at a wavelength of 236 nm.

Example 3

Preparation of an Ibuprofen Fill Matrix

A hydrophilic vehicle-based dual controlled-release matrix system was prepared containing the following ingredients

| Name of the ingredient | % wt. of fill matrix |
|---|---|
| Polyethylene glycol | 42 |
| Hypromellose | 3.5 |
| CARBOPOL ® 972P | 1 |
| PVP90M | 1 |
| Ibuprofen | 52.5 |

Figure 3:
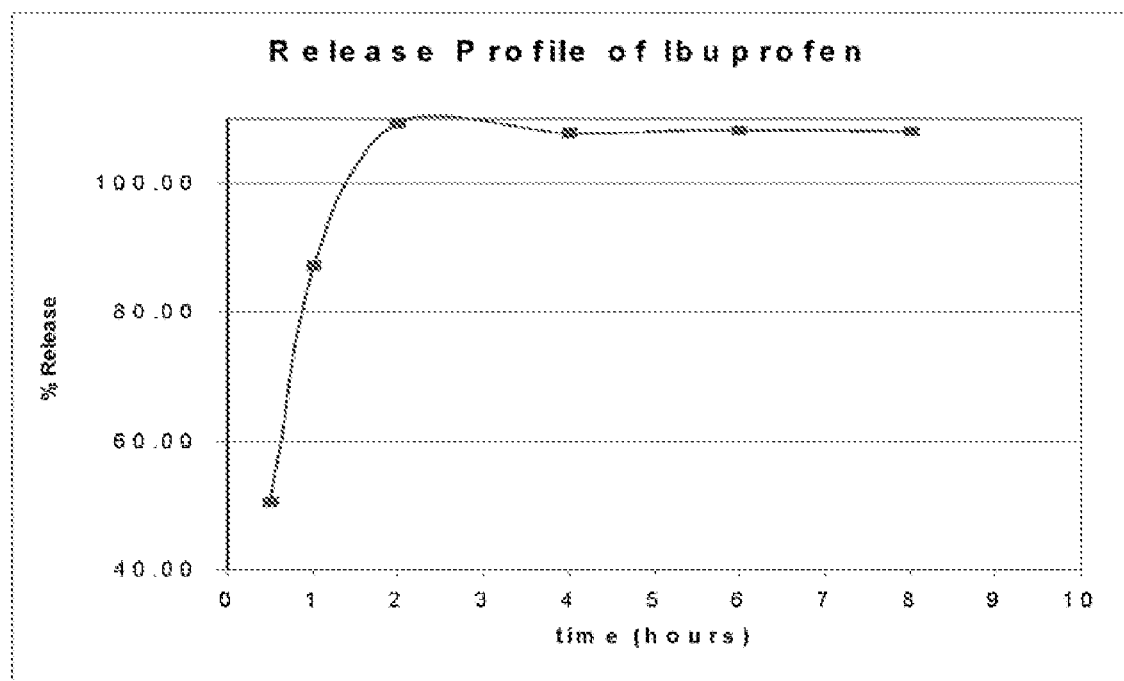
FIG. 3 show the release profile of Ibuprofen (% ibuprofen) versus time (hours) from a hydrophilic vehicle-based matrix system.
Figure 4:
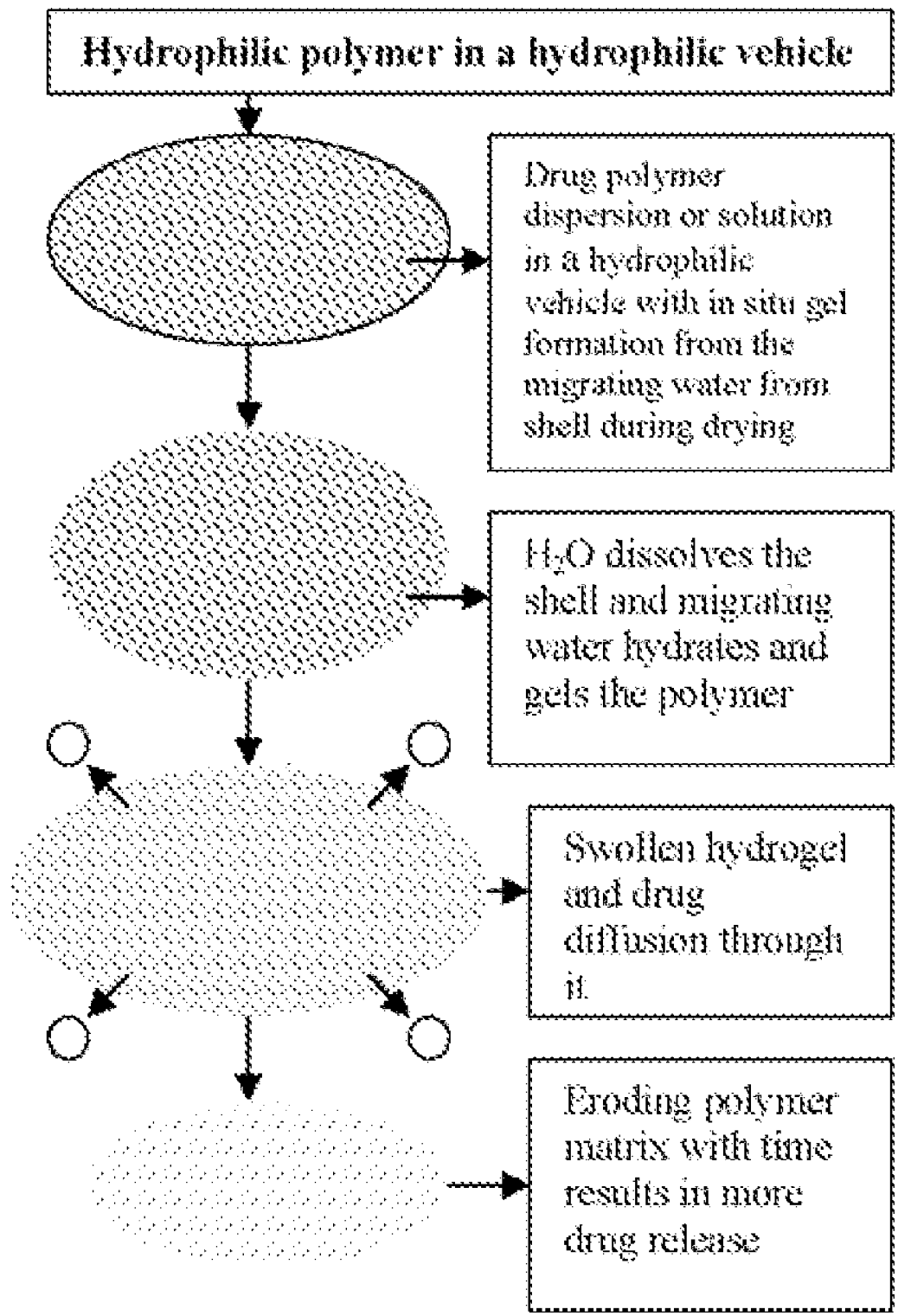
FIG. 4 is a schematic showing the mechanism of drug release from a hydrophilic vehicle-based matrix.

In vitro drug release studies were conducted using a USP dissolution apparatus II (paddles) at 100 rpm. The results are shown in FIG. 3. Experiments were conducted in dissolution media at a temperature of 37.0±0.5° C. for 8 hours in 7.2 phosphate buffer. Samples were periodically withdrawn and analyzed for ibuprofen content using the ultraviolet ("UV") method. The samples were analyzed at a wavelength of 276 nm.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference.

I claim:

1. A capsule comprising a dual controlled release liquid matrix, the matrix comprising:
   (a) a primary rate-controlling barrier comprising a hydrophilic vehicle;
   (b) a secondary rate-controlling barrier comprising a hydrogel-forming polymeric material dissolved or dispersed in the hydrophilic vehicle; and
   (c) a therapeutic, prophylactic or diagnostic agent dissolved or dispersed within the liquid matrix,
   wherein when the liquid matrix comes in contact with an aqueous medium, the hydrogel forming material forms a hydrogel suspended in the hydrophilic vehicle, and
   wherein the release of the therapeutic, prophylactic, or diagnostic agent is biphasic.

2. The capsule of claim 1, wherein the secondary rate-controlling barrier is dissolved or dispersed in the primary rate-controlling barrier.

3. The capsule of claim 1, wherein the hydrophilic vehicle is selected from the group consisting of polyethylene glycol, polyoxyethylene 32 lauric glyceride, polyoxyethylene 8 caprylic/capric glyceride, glycofurol and polysorbate.

4. The capsule of claim 1, wherein the hydrophilic vehicle is present in an amount from about 10 to about 80% by weight of the matrix.

5. The capsule of claim 4, wherein the hydrophilic vehicle is present in an amount from about 20 to about 60% by weight of the matrix.

6. The capsule of claim 1, further comprising one or more solvents miscible with the hydrophilic vehicle.

7. The capsule of claim 6, where in the one or more miscible solvents is selected from the group consisting of glycerin, propylene glycol, ethanol, glycofurol and macrogol 8-glyceride.

8. The capsule of claim 6, wherein the one or more miscible solvents is present in an amount from about 1% to about 80% by weight of the fill material.

9. The capsule of claim 1, wherein the hydrogel-forming polymeric material is selected from the group consisting of cellulose ethers, cross-linked acrylates, alginates, guar, xanthan gum, carrageenan, carboxymethyl cellulose, high molecular weight polypyrrolidone, and mixtures thereof.

10. The capsule of claim 1, wherein the hydrogel-forming polymeric material is present in an amount from about 3% to about 80% by weight of the matrix.

11. The capsule of claim 10, wherein the hydrogel-forming polymeric material is present in an amount from about 5% to about 50% by weight of the matrix.

12. The capsule of claim 1, wherein the therapeutically, prophylactic, and diagnostic agent is selected from the group consisting of analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelminthic agents; antihistamines; antihyperlipidemic agents; antihypertensive agents; anti-infective agents; anti-inflammatory agents; antimigraine agents; antineoplastic agents; antiparkinson drugs; antipruritic agents; antipsychotic agents; antipyretic agents; antispasmodic agents; antitubercular agents; antiulcer agents; antiviral agents; anxiolytic agents; appetite suppressants; attention deficit disorder and attention deficit hyperactivity disorder drugs; cardiovascular agents including calcium channel blockers, antianginal agents, central nervous system agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimulants; sedatives; sialagogues, steroids; smoking cessation agents; sympathomimetics; tranquilizers; vasodilators; beta-agonist; tocolytic agents, and combinations thereof.

13. The capsule of claim 1, wherein the therapeutic, prophylactic or diagnostic agent is a drug prone to abuse.

14. The capsule of claim 1, wherein the capsule is selected from the group consisting of soft gelatin capsules, hard gelatin capsules, and non-gelatin soft capsules.

15. The capsule of claim 1, wherein the release of the therapeutic, prophylactic or diagnostic agent is modulated for up to 24 hours.

* * * * *

UNITED STATES PATENT AND TRADEMARK OFFICE
CERTIFICATE OF CORRECTION

| | | |
|---|---|---|
| PATENT NO. | : 8,333,989 B2 | Page 1 of 1 |
| APPLICATION NO. | : 11/553356 | |
| DATED | : December 18, 2012 | |
| INVENTOR(S) | : Sukuru | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 781 days.

Signed and Sealed this
Twenty-eighth Day of October, 2014

Michelle K. Lee
*Deputy Director of the United States Patent and Trademark Office*